US010260148B2

(12) United States Patent
Siu et al.

(10) Patent No.: US 10,260,148 B2
(45) Date of Patent: Apr. 16, 2019

(54) POROUS POLYMERS FOR THE ABATEMENT AND PURIFICATION OF ELECTRONIC GAS AND THE REMOVAL OF MERCURY FROM HYDROCARBON STREAMS

(71) Applicant: NUMAT TECHNOLOGIES, INC., Skokie, IL (US)

(72) Inventors: Paul Wai-Man Siu, Evanston, IL (US); Mitchell Hugh Weston, Chicago, IL (US)

(73) Assignee: NUMAT TECHNOLOGIES, INC., Skokie, IL (US)

( * ) Notice: Subject to any disclaimer, the term of this patent is extended or adjusted under 35 U.S.C. 154(b) by 349 days.

(21) Appl. No.: 14/957,245

(22) Filed: Dec. 2, 2015

(65) Prior Publication Data

US 2016/0160348 A1 Jun. 9, 2016

Related U.S. Application Data

(60) Provisional application No. 62/087,395, filed on Dec. 4, 2014.

(51) Int. Cl.
| | | |
|---|---|---|
| *B01J 20/22* | (2006.01) | |
| *B01J 20/26* | (2006.01) | |
| *C23C 16/44* | (2006.01) | |
| *C07F 1/08* | (2006.01) | |
| *C07F 3/06* | (2006.01) | |
| *C07F 7/00* | (2006.01) | |
| *C23C 16/455* | (2006.01) | |
| *H01L 21/425* | (2006.01) | |

(52) U.S. Cl.
CPC ......... *C23C 16/4402* (2013.01); *B01J 20/226* (2013.01); *B01J 20/26* (2013.01); *C07F 1/08* (2013.01); *C07F 3/06* (2013.01); *C07F 7/003* (2013.01); *C23C 16/4412* (2013.01); *C23C 16/45544* (2013.01); *H01L 21/425* (2013.01); *Y02C 20/30* (2013.01)

(58) Field of Classification Search
CPC .......... B01J 20/22; B01J 20/26; B01J 20/226; C07F 1/08; C07F 3/06; C07F 7/00; C07F 7/003; C23C 16/44; C23C 16/455; C23C 16/4402; C23C 16/4412; C23C 16/45544; H01L 21/425; Y02C 20/30
See application file for complete search history.

(56) References Cited

U.S. PATENT DOCUMENTS

| | | |
|---|---|---|
| 7,799,120 B2 | 9/2010 | Yaghi et al. |
| 2011/0277767 A1 | 11/2011 | Yaghi et al. |
| 2012/0247333 A1 | 10/2012 | Miller |

FOREIGN PATENT DOCUMENTS

| | | |
|---|---|---|
| WO | WO 90/07971 A1 | 7/1990 |
| WO | WO2007128994 A1 | 11/2007 |
| WO | WO2009035664 A1 | 3/2009 |

OTHER PUBLICATIONS

International Search Report and Written Opinion of the International Searching Authority for PCT/US2015/063535, dated Jun. 3, 2016, 27 pages.
Ke. F. et al., "Thiol-functionalization of metal-organic framework by a facile coordination-based postsynthetic strategy and enhanced removal of Hg2+ from water", Journal of Hazardous Materials, vol. 196, pp. 36-43, (Nov. 30, 2011).
Lu, G. et al., "Imparting functionality to a metal-organic framework material by controlled nanoparticle encapsulation", Nature Chemistry, vol. 4, No. 4, pp. 310-316, (Feb. 19, 2012).
Yee, K. K. et al., "Effective mercury sorption by thiol-laced metal-organic frameworks: in strong acid and the vapor phase", J. Am. Chem. Soc., vol. 135, No. 21, pp. 7795-7798, (May 29, 2013).
Ferey, G., Hybrid porous solids: past, present, future. Chemical Society Reviews, 2008. 37(1): p. 191-214.
Farha, O.K., et al., De novo synthesis of a metal-organic framework material featuring ultrahigh surface area and gas storage capacities. Nature Chemistry, 2010. 2(11): p. 944-948.
Ferey, G., et al., A chromium terephthalate-based solid with unusually large pore volumes and surface area. Science, 2005. 309(5743): p. 2040-2042.
Wilmer, C.E., et al., Structure-property relationships of porous materials for carbon dioxide separation and capture. Energy & Environmental Science, 2012. 5(12): p. 9849-9856.
Wu, D., et al., Design and preparation of porous polymers. Chemical Review, 2012, 112(7): p. 3959.
Farha, O.K., et al., Metal-Organic Framework Materials with Ultrahigh Surface Areas: Is the Sky the Limit? Journal of the American Chemical Society, 2012, 134(36): p. 15016-15021.
Li, J., et al, Selective gas adsorption and separation in metal-organic frameworks. Chemical Society Review, 2009, 38: p. 1477-1504.
Lu, W., et al., Porous Polymer Networks: Synthesis, Porosity, and Applications in Gas Storage/Separation. Chemistry of Materials, 2010, 22(21): p. 5964-5972.
Weston, M. H., et al., Phosphine Gas Adsorption in a Series of Metal-Organic Frameworks. Inorganic Chemistry, 2015, 54(17): p. 8162-8164.
Li, H. et al., Design and Synthesis of an Exceptionally Stable and Highly Porous Metal-Organic Framework, Nature, vol. 402, pp. 276-279, (1999).

(Continued)

*Primary Examiner* — Irina S Zemel
(74) *Attorney, Agent, or Firm* — The Marbury Law Group PLLC

(57) ABSTRACT

A porous material, including metal organic frameworks (MOFs) and porous organic polymer (POP), with reactivity with or sorptive affinity towards (a) electronic gas to substantially remove or abate electronic gas in an electronic gas-containing effluent, or (b) contaminants in a stream of electronic gas to substantially remove the contaminants from a stream of electronic gas and increase the purity of said electronic gas, or (c) trace mercury contaminant in a hydrocarbon stream to substantially remove said mercury contaminant and increase the purity of said hydrocarbon stream. MOFs are the coordination product of metal ions and multidentate organic ligands, whereas POPs are the product of polymerization between organic monomers.

10 Claims, 5 Drawing Sheets

(56) References Cited

OTHER PUBLICATIONS

Furukawa, H., et al., Ultrahigh Porosity in Metal-Organic Frameworks. Science, 2010. 329(5990): p. 424-428.
Wilmer, C.E., et al., Large-scale screening of hypothetical metal-organic frameworks. Nature Chemistry, 2012. 4(2): p. 83-89.
Nelson, A.P., et al., Supercritical Processing as a Route to High Internal Surface Areas and Permanent Microporosity in Metal-Organic Framework Materials. Journal of the American Chemical Society, 2009, 131(2): p. 458.
Chae, H.K., et al., A route to high surface area, porosity and inclusion of large molecules in crystals. Nature, 2004. 427(6974): p. 523-527.
International Preliminary Report on Patentability and Written Opinion of the International Searching Authority for International Patent Application No. PCT/US2015/063535, dated Jun. 15, 2017, 23 pages.
Office Communication, Extended European Search Report for European Patent No. 15864849.3, dated May 17, 2018, 9 pages.
Li, J.R. et al., "Selective Gas Adsorption and Separation in Metal-Organic Frameworks," Critical Review, Chemical Society Reviews, vol. 38, pp. 1477-1504, (2009).
European Office Action Communication Pursuant to Article 94(3) EPC for European Patent Application No. 15864849.3, dated Mar. 1, 2019, 6 pages.

(MOF-5)

($M_2$(DOBDC))

(Cu-BTC)

(UiO-66-SH)

(UiO-66)

FIG. 1F    MOF    metal-containing solution
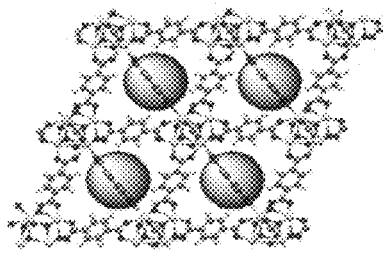
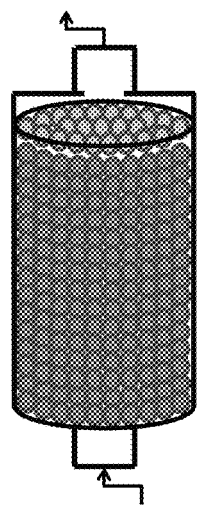
FIG. 2A  Pellet-filled container
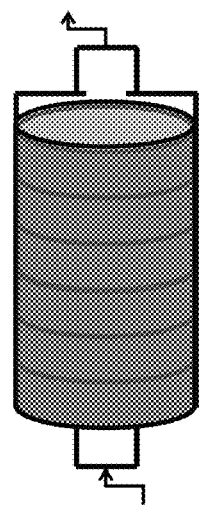
FIG. 2B  Disk-filled container
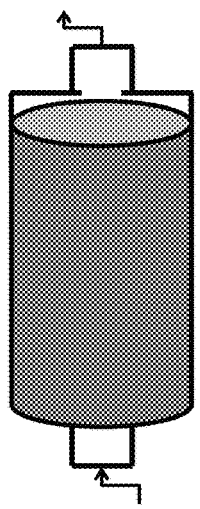
FIG. 2C  Monolithic MOF-filled container

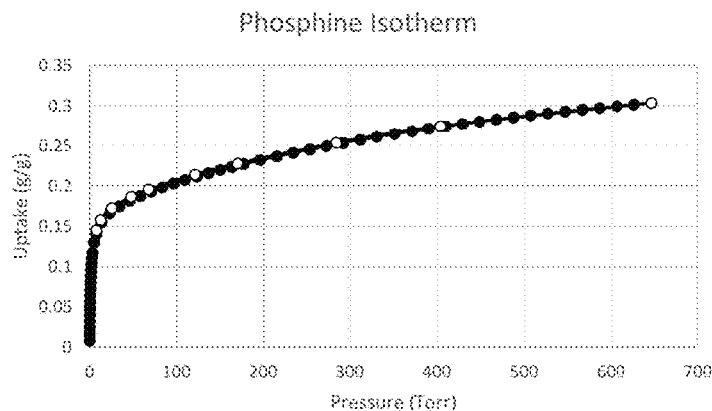
FIG. 3A  Mn₂(DOBDC) Phosphine Isotherm
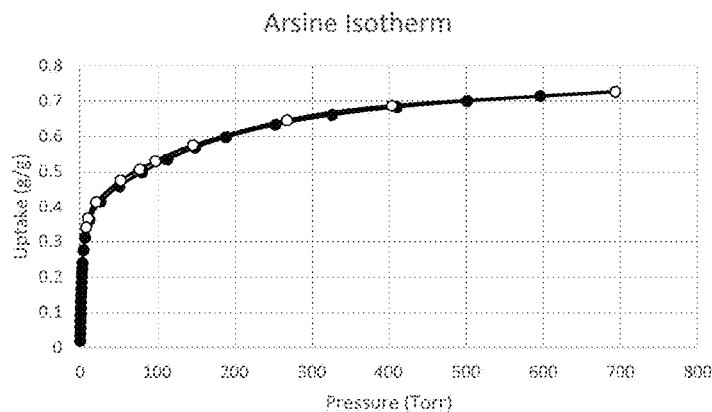
FIG. 3B  Mn₂(DOBDC) Arsine Isotherm
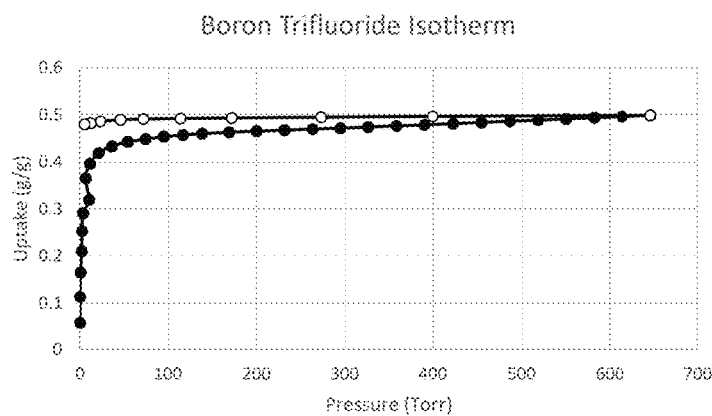
FIG. 3C  Co₂(DOBDC) Boron Trifluoride Isotherm

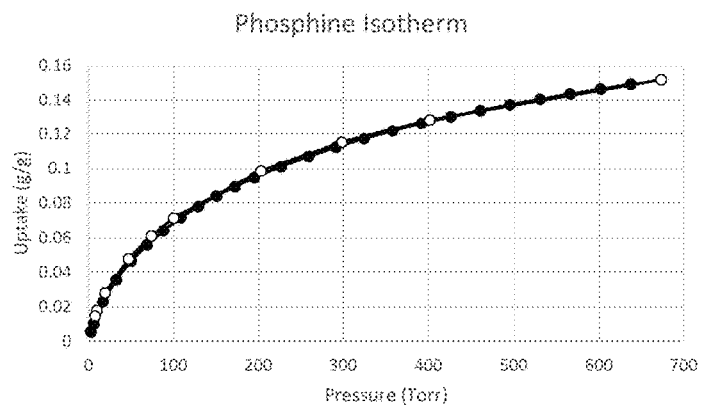
FIG. 4A  PAF-40 Phosphine Isotherm
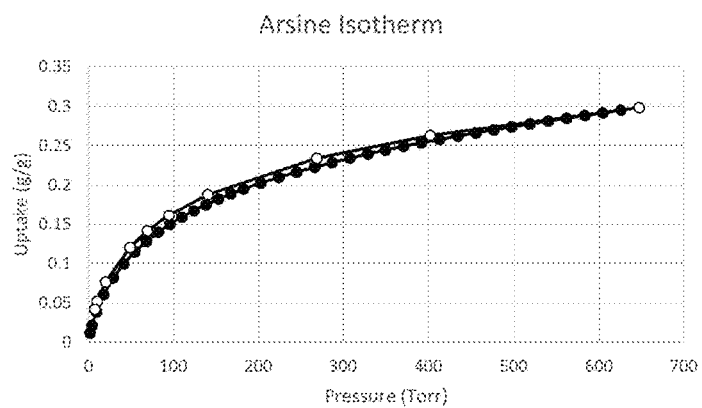
FIG. 4B  PAF-40 Arsine Isotherm
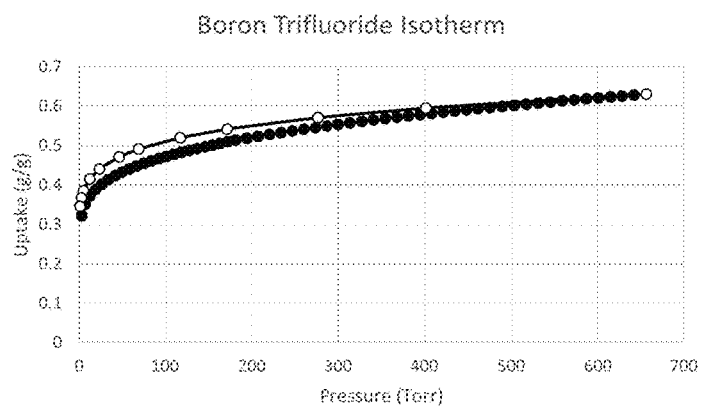
FIG. 4C  PAF-40 Boron Trifluoride Isotherm

POROUS POLYMERS FOR THE ABATEMENT AND PURIFICATION OF ELECTRONIC GAS AND THE REMOVAL OF MERCURY FROM HYDROCARBON STREAMS

FIELD

The present invention relates to porous polymers, including metal organic frameworks and porous organic polymers, for (a) the abatement and purification of electronic gas, and (b) the removal of mercury from hydrocarbon streams.

BACKGROUND

The purification of gas streams is a critical component of many processes, including hydrocarbon gas production and semiconductor manufacturing.

Low quantities of undesirable mercury components are known to exist naturally in geological hydrocarbon sources, particularly for natural gases. Hydrocarbons may include alkanes, such as methane, ethane, propane, butane, pentane, hexane, etc, alkenes and alkynes. The alkanes, alkenes and alkynes may be liner, branched or cyclic. The exposure of aluminum-based equipment in natural gas processing plants to large volumes of trace mercury results in cumulative amalgamate formation, which can lead to corrosive cracking and equipment failure. There are also environmental and health concerns over the discharge of hazardous mercury contaminates, with regulations requiring the complete removal of mercury compounds from fuel-grade gas.

Current methods of removing trace mercury from hydrocarbon streams involve reactions of mercury with chemicals that are often supported on porous materials such as activated carbon, alumina, silica and zeolite. In semiconductor manufacturing, the purity of electronic gases used for the fabrication of solid state devices, such as transistors, diodes, light emitting diodes, lasers, solar cells, and capacitors, is important. As used herein, "electronic gases" are source gases used for doping (e.g. ion implantation, chemical vapor deposition (CVD), atomic layer deposition (ALD)) or layer deposition of semiconductor (e.g. Group IV, III-V, II-VI), insulators (e.g. silicon oxide, silicon nitride) and conductors (e.g. tungsten) in solid state devices. It is understood that trace quantities of electronic gas contaminates can have significant detrimental effects on the quality of semiconductor devices. These contaminates are commonly gaseous compounds that include acids, ammonia, amines, alcohols, carbon dioxide, carbon monoxide, hydrocarbons, hydrogen, hydrogen sulfides, nitrogen oxides, oxygen, siloxanes, sulfur dioxide, sulfur oxides and water. In particular, there is interest in the vigorous purification of hydride gases used in semiconductor manufacturing, such as ammonia, arsine, phosphine, diborane, disilane, germane and silane and other gases such as boron trifluoride. Current methods of hydride gas purification focus on the use of reduced metal and metal oxides. Large excess amounts of electronic gases are commonly used during the layer deposition of semiconductors, insulators, and conductors, which necessitates the removal of leftover unreacted electronic gases. Particularly for hydride gases, current conventional electronic gas abatement systems rely on dry scrubbers comprising of metal oxides, metal carbonates, and metal hydroxides.

Across all aforementioned applications of purification and abatement, the use of traditional porous materials, such as activated carbon, alumina, silica and zeolites, have shown to benefit the efficiency and reactivity of the active metal and non-metal components. It is understood that the available contact surface area of the active component is greatly increased when either mixed-in or supported onto these porous materials, enhancing the overall diffusion characteristics of these sorbents. However, further benefits and enhancements have been limited by the relatively low porosity and poor customizability of these porous materials. The ill-defined internal structure and irregular porosity for some of these materials also hampers performance

SUMMARY

Embodiments of the invention are drawn to (a) the development of novel MOF materials comprising the coordination product of a plurality of metal nodes or clusters, each metal cluster comprising one or more metal ions, and a plurality of multidentate organic ligands that connect adjacent metal clusters, wherein the metal ion and the organic ligand are selected to provide reactivity with or sorptive affinity towards electronic gas to substantially remove or abate electronic gas in an electronic gas-containing effluent, (b) the abatement of phosphine, arsine, or boron trifluoride using a MOF with open coordination sites comprises at least two metal ions (of oxidation state of 2+) or a combination of two metal ions (of 2+ oxidation state) and one of the organic ligands are made with the precursors of dihydroxyterepthalic acid, (c) the abatement of boron trifluoride using a MOF comprising of at least one metal cluster with paddle-wheel geometry containing at least a $Cu^{2+}$ metal ion with a free coordination site and at least one of the organic ligands is made with the precursor trimesic acid, and (d) the integration of MOF material into an abatement system, enabling the electronic gas-containing effluent to flow in contact with the MOF material to substantially decrease the concentration of said electronic gas in the effluent.

Another embodiment relates to (a) the development of novel POP materials comprising the polymerization product from at least a plurality of organic monomers, wherein the organic monomers are selected to provide reactivity with or sorptive affinity toward electronic gas to substantially remove or abate electronic gas in an electronic gas-containing effluent, (b) the abatement of phosphine, arsine, or boron trifluoride using a POP comprising the polymerization product of aromatic monomers, and (c) the integration of POP material into an abatement system, enabling the electronic gas-containing effluent to flow in contact with the MOF material to substantially decrease the concentration of said electronic gas in the effluent.

Another embodiment relates to (a) the development of novel MOFs comprising the coordination product of a plurality of metal clusters, each metal cluster comprising one or more metal ions, and a plurality of multidentate organic ligands that connect adjacent metal clusters, wherein the metal ion and the organic ligand are selected to provide reactivity with or sorptive affinity towards contaminants in a stream of electronic gas to substantially remove the contaminants from a stream of electronic gas and increase the purity of said electronic gas, and (b) the integration of MOF material into a purification system, enabling a stream of electronic gas to flow in contact with the MOF material to substantially remove the contaminants from the stream of electronic gas and increase the purity of said electronic gas.

Another embodiment relates to (a) the development of novel POP comprising the polymerization product from at least a plurality of organic monomers, wherein the organic monomers are selected to provide reactivity with or sorptive affinity towards contaminants in a stream of electronic gas to substantially remove the contaminants from a stream of electronic gas and increase the purity of said electronic gas, and (b) the integration of POP material into a purification system, enabling a stream of electronic gas to flow in contact with the POP material to substantially remove the contaminants from the stream of electronic gas and increase the purity of said electronic gas.

Another embodiment related to (a) the development of novel MOF materials comprising the coordination product of a plurality of metal clusters, each metal cluster comprising one or more metal ions, and a plurality of multidentate organic ligands that connect adjacent metal clusters, wherein the metal ion and the organic ligand are selected to provide reactivity with or sorptive affinity toward trace mercury contaminant in a hydrocarbon stream to substantially remove said mercury contaminant and increase the purity of said hydrocarbon stream, (b) a novel MOF material comprising at least one $Zr^{4+}$ metal ion with at least one of the organic ligand that is made with the precursor terephthalic acid, and another organic ligand that is made with the precursor thioglycolic acid, salts of thioglycolic acid, and combinations thereof, and (c) a novel MOF material comprising at least one $Zr^{4+}$ metal ion with at least one of the organic ligands that is made with the precursor terephthalic acid and encapsulates silver that is capable of forming an amalgam with mercury, and (d) the integration of MOF material into a purification system, enabling a hydrocarbon stream to flows in contact with the MOF material to substantially remove the mercury contaminants from the hydrocarbon stream and increase the purity of said hydrocarbon stream.

Another embodiment related to (a) the development of novel POP material comprising the polymerization product from at least a plurality of organic monomers, wherein the organic monomers are selected to provide reactivity with or sorptive affinity towards trace mercury contaminant in a hydrocarbon stream to substantially remove said mercury contaminant and increase the purity of said hydrocarbon stream, and (b) the integration of POP material into a purification system, enabling a hydrocarbon stream to flows in contact with the POP material to substantially remove the mercury contaminants from the hydrocarbon stream and increase the purity of said hydrocarbon stream.

BRIEF DESCRIPTION OF THE DRAWINGS

FIGs. 1A-F illustrate the representative formation and structure of metal organic frameworks including FIG. 1A: MOF-5, FIG. 1B: $M_2$(DOBDC), FIG. 1C: Cu-BTC, FIG. 1D: UiO-66-SH, FIG. 1E: UiO-66, and FIG. 1F: a generic MOF with metal encapsulation.

FIG. 2A is a schematic illustration of an abatement and purification system with a pellet-filled container of MOFs or POPs, FIG. 2B is a schematic illustration of an abatement and purification system with a disk-filled container of MOFs or POPs and FIG. 2C is a schematic illustration of an abatement and purification system with a monolithic MOF-filled container of MOFs or POPs.

FIG. 3A is a plot illustrating the abatement capacity of $PH_3$ in $Mn_2$(DOBDC) as a function of pressure, FIG. 3B is a plot illustrating the abatement capacity of $AsH_3$ in $Mn_2$(DOBDC) as a function of pressure and FIG. 3C is a plot illustrating the abatement capacity of $BF_3$ in $Co_2$(DOBDC) as a function of pressure.

FIG. 4A is a plot illustrating the abatement capacity of $PH_3$ in PAF-40 as a function of pressure, FIG. 4B is a plot illustrating the abatement capacity of $AsH_3$ in PAF-40 as a function of pressure and FIG. 4C is a plot illustrating the abatement capacity of $BF_3$ in PAF-40 as a function of pressure.

DETAILED DESCRIPTION

Figure 1A:
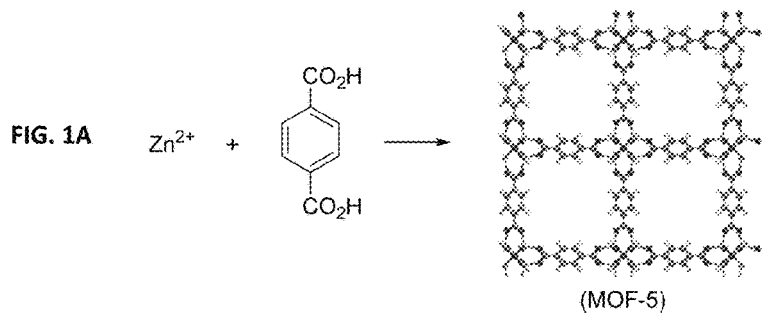

It is generally strongly desired in purification and abatement to maximize the flow rate and concentration of the gas stream while maintaining or reducing the size of the sorbent system.

It would therefore be a significant advance in the art to provide a high-performance porous material for the effective abatement of electronic gas from an electronic gas-containing effluent. It would also be advantageous to provide a high-performance porous material for the effective removal of contaminates from a stream of electronic gas. It would also be advantageous to provide a high-performance porous material for the removal of mercury from hydrocarbon gas streams.

Extensive research over the past few years has focused on the synthesis and characterization of microporous materials with high internal surface area, which is a measurement of internal porosity.

Metal-Organic Frameworks (MOFs), a crystalline subset of microporous materials, have shown promise in a wide range of applications from gas storage and separation applications as discussed in Li, H., et al., Design and synthesis of an exceptionally stable and highly porous metal-organic framework. Nature, 1999. 402(6759): p. 276-279; Ferey, G., Hybrid porous solids: past, present, future. Chemical Society Reviews, 2008. 37(1): p. 191-214 and Wilmer, C. E., et al., Large-scale screening of hypothetical metal-organic frameworks. Nature Chemistry, 2012. 4(2): p. 83-89, hereby incorporated by reference in their entirety. MOFs are the coordination product of metal ions and multidentate organic ligands (FIGS. 1A-f). Metal ions of MOFs include, but are not limited to, $Li^+$, $Na^+$, $K^+$, $Rb^+$, $Be^{2+}$, $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{5+}$, $V^{4+}$, $V^{3+}$, $Nb^{3+}$, $Ta^{3+}$, $Cr^{3+}$, $Cr^{2+}$, $Mo^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Al^{3+}$, $Ga^{3+}$, $In^{3+}$, $Si^{4+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, $Cd^{2+}$, $Mn^{2+}$, $Tb^{3+}$, $Gd^{3+}$, $Ce^{3+}$, $La^{3+}$ and $Cr^{4+}$, and combinations thereof.

The accelerated development of MOFs for gas storage and separation in the past decade are attributed to their favorable performance characteristics, such as structural diversity, well-defined internal structures, synthetic customizability, high surface area, porosity, and stability as discussed in Wilmer, C. E., et al., Large-scale screening of hypothetical metal-organic frameworks. Nature Chemistry, 2012. 4(2): p. 83-89;

Farha, O. K., et al., De novo synthesis of a metal-organic framework material featuring ultrahigh surface area and gas storage capacities. Nature Chemistry, 2010. 2(11): p. 944-948; Furukawa, H., et al., Ultrahigh Porosity in Metal-Organic Frameworks. Science, 2010. 329(5990): p. 424-4281 Ferey, G., et al., A chromium terephthalate-based solid with unusually large pore volumes and surface area. Science, 2005. 309(5743): p. 2040-2042; Chae, H. K., et al., A route to high surface area, porosity and inclusion of large molecules in crystals. Nature, 2004. 427(6974): p. 523-527 and Wilmer, C. E., et al., Structure-property relationships of porous materials for carbon dioxide separation and capture. Energy & Environmental Science, 2012. 5(12): p. 9849-9856, hereby incorporated by reference in their entirety.

Porous organic polymers (POPs) are the product of polymerization between organic monomers that also exhibit favorable performance characteristics for gas storage and separation, owing to their high surface area, porosity, extreme stability, and short-range crystallinity, as discussed in Wu, D., et al., Design and preparation of porous polymers. Chemical Review, 2012, 112(7): p. 3959, hereby incorporated by reference in its entirety.

The favorable characteristics of MOFs and POPs make them ideal candidates for the abatement and purification of electronic gas, as well as the removal of mercury from hydrocarbon streams.

Traditional lower-performing porous materials, such as activated carbon, alumina, silica and zeolite, have typically been used as support materials to enhance the contact surface area of the active metal and non-metal components in the abatement and purification of electronic gas, as well as the removal of mercury from hydrocarbon streams. In general, there is a positive correlation between the contact surface area of the active component and the overall efficiency and reactivity of these sorbent systems. The diffusion characteristic of these sorbent material is also tightly tied to porosity of the materials used.

Typically, activated carbon, alumina, silica and zeolites exhibit relatively low surface area, which is representative of their low porosity. For example, one of the highest surface areas reported for activated carbon and zeolite are at 2,000 $m^2/g$ and 900 $m^2/g$, respectively. In contrast, the current surface area record reported for POPs is 5,000 $m^2/g$ and for MOF materials is at 7,000 $m^2/g$. It is believed that MOFs with surface area upward of 14,500 $m^2/g$ can be accessed, as discussed in Farha, O. K., et al., Metal-Organic Framework Materials with Ultrahigh Surface Areas: Is the Sky the Limit? Journal of the American Chemical Society, 2012, 134(36): p. 15016-15021 and Nelson, A. P., et al., Supercritical Processing as a Route to High Internal Surface Areas and Permanent Microporosity in Metal-Organic Framework Materials. Journal of the American Chemical Society, 2009, 131(2): p. 458, hereby incorporated by reference in their entirety. The higher surface area and porosity make MOFs and POPs superior classes of porous material for abatement and purification applications.

Furthermore, MOFs and POPs offer greater degree of design flexibility than traditional porous materials. MOFs also exhibit well-defined internal pore structures, contrasting activated carbon. This enables a bottom-up approach to tailor design MOFs and POPs with sorptive affinity or reactivity for specific gases and components of interest in abatement and purification applications. Although both classes of materials have shown promises in many areas of gas storage and separation, including natural as storage and purification, as discussed in Li, J., et al, Selective gas adsorption and separation in metal-organic frameworks. Chemical Society Review, 2009, 38: p. 1477-1504 and Lu, W., et al., Porous Polymer Networks: Synthesis, Porosity, and Applications in Gas Storage/Separation. Chemistry of Materials, 2010, 22(21): p. 5964-5972, hereby incorporated by reference in their entirety, the viability of these advanced materials for the abatement and purification of electronic gases in semiconductor manufacturing has largely been ignored.

Embodiments of the present invention includes synthesized MOFs and POPs with reactivity with or sorptive affinity towards (a) electronic gas to substantially remove or abate electronic gas in an electronic gas-containing effluent, or (b) contaminants in a stream of electronic gas to substantially remove the contaminants from a stream of electronic gas and increase the purity of said electronic gas, or (c) trace mercury contaminant in a hydrocarbon stream to substantially remove said mercury contaminant and increase the purity of said hydrocarbon stream.

The present invention relates to electronic gas that is selected from a group consisting of ammonia, arsine, boron trichloride, boron trifluoride, carbonyl sulfide, chlorine, deuterium, diborane, dichlorosilane, dichlorosilane, difluoromethane, disilane, fluorine, germane, germanium tetrafluoride, hexafluoroethane, hydrogen bromide, hydrogen chloride, hydrogen fluoride, hydrogen selenide, hydrogen telluride, hydrogen sulfide, methyl fluoride, methyl silane, neon, nitric organic, nitrogen trifluoride, perfluoropropane, phosphine, silane, silicon tetrachloride, tetrafluoromethane, tetramethylsilane, silicon tetrafluoride, stibine, sulfur hexafluoride, trichlorosilane, trifluoromethane, trimethylsilane, tungsten hexafluoride, acetylene, organometallic gaseous reagents, and combinations thereof.

Electronic Gas Abatement

In one embodiment, the present invention relates a MOF or a POP that reacts with electronic gas in an electronic gas-containing effluent through reaction mechanism comprising oxidation, reduction, hydrolysis, formation of dative bond, and combinations thereof. The advantage of a bottom-up approach to tailor designing MOFs and POPs enables the incorporation of functional groups that are reactive with electronic gas into porous materials by selecting the organic ligand or organic monomer with reactive functional groups as building blocks. High density of reactive sites can be achieved through this approach which results in an electronic gas abatement material with high reactivity, efficiency, and favorable diffusion characteristics.

In another embodiment, the present invention relates to a MOF or a POP that encapsulates a chemical specie that is reactive toward electronic gas, wherein the chemical specie is selected from a group consisting of basic species, acidic species, hydrolyzing species, oxidants, reductants, and combinations thereof. The basic specie is selected from metal hydroxide, metal carbonate, and combinations thereof, wherein the metal is selected from a group consisting of lithium, sodium, potassium, rubidium, cesium, beryllium, magnesium, calcium, strontium, barium, yttrium, zirconium, vanadium, chromium, manganese, iron, cobalt, nickel, palladium, platinum, copper, silver, gold, zinc, cadmium, mercury, aluminum, indium, thallium, lead, bismuth, and combinations thereof. The oxidant is a metal oxide comprises of metal that is selected from a group consisting of lithium, sodium, potassium, rubidium, cesium, beryllium, magnesium, calcium, strontium, barium, scandium, yttrium, titanium, zirconium, hafnium, vanadium, niobium, tantalum, chromium, molybdenum, tungsten, manganese, rhenium, iron, ruthenium, osmium, cobalt, rhodium, iridium, nickel, palladium, platinum, copper, silver, gold, zinc, cadmium, mercury, aluminum, gallium, indium, thallium, tin, lead, bismuth, and combinations thereof. The use of metal hydroxides, metal carbonate and metal oxides in the conventional electronic gas abatement systems is well-established; however, their current performances are severely limited by the often necessary accompanied used of porous materials such as activated carbon, alumina, silica, and zeolite. The encapsulation these reactive chemical species within pores of highly porous MOF and POP materials enables a substantial increase in the contact surface area of these active components.

In another embodiment, the metal cluster and the organic ligand are selected to provide a MOF that reacts with a hydrolyzing specie to generate a reaction product that reacts with electronic gas. Certain structural motifs for MOFs, such as those comprising of $Zn_4O$ metal clusters, are known to react with water and other hydrolyzing reagents to generate zinc oxide, which is an active component in the abatement of electronic gases, including hydride gases. An example of a MOF comprising of $Zn_4O$ metal clusters is MOF-5 (FIG. 1A) Similarly, the organic monomer can be selected to provide a POP that reacts with a hydrolyzing specie to generate a reaction product that reacts with electronic gas.

The present invention relates to a MOF comprised of metal clusters, each metal cluster comprising one or more metal ions where each metal is either fully saturated having no open coordination sites or at least one metal in the cluster has a free coordination site. In one embodiment, the free coordination site can react with electronic gas through formation of dative bond, thus offering an additional and potentially synergistic mechanism of abatement.

Figure 1B:
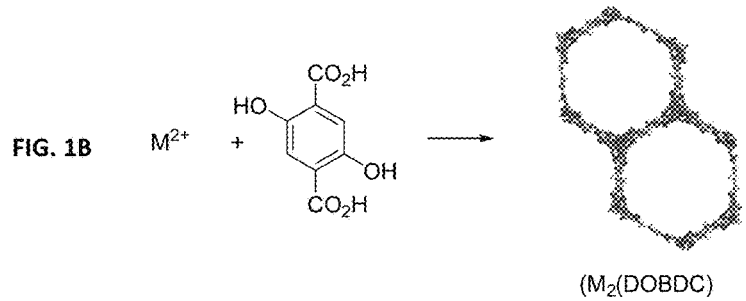

An embodiment of the present invention relates to a MOF with open coordination sites comprises at least two metal ions (of oxidation states of 2+) and one of the organic ligands are made with the precursors of dihydroxyterepthalic acid (as shown in FIG. 1B), wherein the MOF has a gravimetric uptake capacity for arsine of at least 0.35 gram of arsine per gram of MOF measured at 650 torr and 25° C. For example, $Mn_2(DOBDC)$ (FIG. 3B) was experimentally exposed to an atmosphere of arsine up to 650 torr at 25° C. and showed an uptake capacity of 0.72 gram of arsine per gram of MOF.

In another embodiment, a MOF with open coordination sites comprises at least two metal ions (of oxidation state of 2+) or a combination of two metal ions (of 2+ oxidation state) and one of the organic ligands are made with the precursors of dihydroxyterepthalic acid (as shown in FIG. 1B), wherein the MOF has a gravimetric uptake capacity for phosphine of at least 0.10 gram of arsine per gram of MOF measured at 650 torr and 25° C. For example, $Mn_2(DOBDC)$ (as shown in FIG. 3A) was experimentally exposed to an atmosphere of phosphine up to 650 torr at 25° C. and showed an uptake capacity of 0.30 gram of phosphine per gram of MOF.

In another embodiment, a MOF with open coordination sites comprises at least two metal ions (of oxidation state of 2+) or a combination of two metal ions (of 2+ oxidation state) and one of the organic ligands are made with the precursors of dihydroxyterepthalic acid (as shown in FIG. 1B), wherein the MOF has a gravimetric uptake capacity for boron trifluoride of at least 0.2 gram of boron trifluoride per gram of MOF measured at 650 torr and 25° C. For example, $Co_2(DOBDC)$ (as shown in FIG. 3C) was experimentally exposed to an atmosphere of boron trifluoride up to 650 torr at 25° C. and showed an uptake capacity of 0.50 gram of boron triflouride per gram of MOF.

Figure 1C:
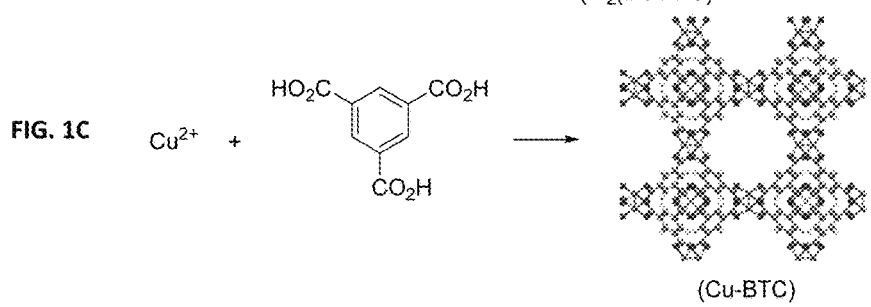

In one embodiment, a MOF comprises at least one metal cluster with paddle-wheel geometry containing at least a $Cu^{2+}$ metal ion with a free coordination site and at least one of the organic ligands is made with the precursor trimesic acid, wherein the MOF has a gravimetric uptake capacity for boron trifluoride of at least 0.35 gram of boron trifluoride per gram of MOF measured at 650 torr and 25° C. For example, Cu-BTC (as shown in FIG. 1C) was experimentally exposed to an atmosphere of boron trifluoride up to 650 torr at 25° C. and showed an uptake capacity of 0.65 gram of boron trifluoride per gram of MOF.

In another embodiment, a MOF comprises at least one metal cluster with paddle-wheel geometry containing at least a $Cu^{2+}$ metal ion with a free coordination site and at least one of the organic ligands is made with the precursor trimesic acid, wherein the MOF has a gravimetric uptake capacity for germanium tetrafluoride of at least 0.80 gram of germanium tetrafluoride per gram of MOF measured at 650 torr and 25° C. For example, Cu-BTC was experimentally exposed to an atmosphere of germanium tetrafluoride up to 650 torr at 25° C. and showed an uptake capacity of 0.95 gram of germanium tetrafluoride per gram of MOF.

In one embodiment, a POP comprising the polymerization product of aromatic monomers, wherein the POP has a gravimetric uptake capacity for phosphine of at least 0.05 gram of phosphine per gram of POP and at most 1.0 gram of phosphine per gram of POP measured at 650 torr and 25° C. For example, PAF-40 was experimentally exposed to an atmosphere of phosphine up to 650 torr at 25° C. and showed an uptake capacity of 0.15 gram of phosphine per gram of POP (as shown in FIG. 4A).

In another embodiment, a POP comprising the polymerization product of aromatic monomers, wherein the POP has a gravimetric uptake capacity for arsine of at least 0.05 gram of arsine per gram of POP and at most 1.0 gram of arsine per gram of POP measured at 650 torr and 25° C. For example, PAF-40 was experimentally exposed to an atmosphere of arsine up to 650 torr at 25° C. and showed an uptake capacity of 0.3 gram of arsine per gram of POP (as shown in FIG. 4B).

In another embodiment, a POP comprising the polymerization product of aromatic monomers, wherein the POP has a gravimetric uptake capacity for boron trifluoride of at least 0.05 gram of boron trifluoride per gram of POP and at most 1.0 gram of boron trifluoride per gram of POP measured at 650 torr and 25° C. For example, PAF-40 was experimentally exposed to an atmosphere of boron trifluoride up to 650 torr at 25° C. and showed an uptake capacity of 0.6 gram of boron trifluoride per gram of POP (as shown in FIG. 4C).

In one embodiment, the MOFs, POPs, and combinations thereof is provided in container through which electronic gas-containing effluent flows in contact with the MOF material to substantially decrease the concentration of said electronic gas in the effluent to below 1 ppm. The porous abatement material can also be provided in multiple beds in conjunction with other materials selected to provide reactivity with or sorptive affinity toward electronic gas to substantially remove or abate electronic gas in an electronic gas-containing effluent. The MOFs or POPs provided in the container can be formed in various shapes, such as pellets (as shown in FIG. 2A), disks (as shown in FIG. 2B), or a monolithic body (as shown in FIG. 2C), in a method that gives optimal diffusion characteristics, reactivity, and efficiency for electronic gas abatement.

Purification of Electronic Gas

In one embodiment, the present invention relates a MOF or a POP that reacts with contaminants in a stream of electronic gas through reaction mechanism consisting of oxidation, reduction, hydrolysis, formation of dative bond, and combinations thereof. The advantage of bottom-up approach to tailor design MOFs and POPs enables the ease of incorporating functional groups that are reactive with electronic gas into porous materials by selecting the organic ligand or organic monomer with reactive functional groups as building blocks. High density of reactive sites can be achieved through this approach which would result in electronic gas abatement material with high reactivity, efficiency, and favorable diffusion characteristics.

The present invention relates to contaminants in a stream of electronic gas, wherein the contaminant is selected from a group consisting of gaseous compounds including, but not limited to acids, ammonia, amines, alcohols, carbon dioxide, carbon monoxide, hydrocarbons, hydrogen, hydrogen sulfides, nitrogen oxides, oxygen, siloxanes, sulfur dioxide, sulfur oxides, water, and combinations thereof.

In another embodiment, the present invention relates a MOF or and a POP that encapsulates chemical specie that is reactive towards contaminants, wherein the chemical specie is selected from a group consisting of basic species, acidic species, hydrolyzing species, oxidants, reductants, and combinations thereof. The encapsulation these reactive chemical species within pores of highly porous MOF and POP materials enables a substantial increase in the contact surface area of these active components.

In another embodiment, the metal cluster and the organic ligand are selected to provide a MOF that reacts with a hydrolyzing specie to generate a reaction product that reacts with contaminant in a stream of electronic gas Similarly, the organic monomer can be selected to provide a POP that reacts with a hydrolyzing specie to generate a reaction product that reacts with contaminants.

The present invention relates to a MOF comprised of metal clusters, each metal cluster comprising one or more metal ions where each metal is either fully saturated having no open coordination sites or at least one metal in the cluster has a free coordination site. In one embodiment, the free coordination site can react with contaminants through formation of dative bonds, thus offering an additional and potentially synergistic mechanism of electronic gas purification.

In one embodiment, the MOFs, POPs, and combinations thereof are provided in a container through which a stream of electronic gas flows in contact with the porous material to substantially remove the contaminants from the stream of electronic gas and increase the purity of said electronic gas. The electronic gas dispensed from the container contains less than 1 ppm of trace contaminants including, but not limited to acids, ammonia, amines, alcohols, carbon dioxide, carbon monoxide, hydrocarbons, hydrogen, hydrogen sulfides, nitrogen oxides, oxygen, siloxanes, sulfur dioxide, sulfur oxides, water, and combinations thereof. The porous abatement material can also be provided in multiple beds in conjunction with other materials that is selected to provide reactivity with or sorptive affinity towards contaminants in a stream of electronic gas and increase the purity of said electronic gas. The MOFs or POPs provided in the container can be formed in various shapes, such as pellets (FIG. 2A), disks (FIG. 2B), or a monolithic body (FIG. 2C), in a method that gives optimal diffusion characteristics, reactivity, and efficiency for electronic gas purification.

Mercury Removal from Hydrocarbon Streams

In one embodiment, the present invention relates to a MOF that reacts with trace mercury contaminant in a hydrocarbon stream, wherein at least one of the organic ligands in the MOF contains at least one chalcogen that is selected from selenium, tellurium, and combinations thereof. It is understood that mercury binds strongly with heavy chalcogens such as sulfur, selenium, and tellurium. Yee et al. describe the mercury uptake of thio-laced MOFs comprised of 2,5-dimercapto-1,4-benzenedicarboxylate ligands that connects adjacent metal clusters, wherein the metal ions are either $Al^{3+}$ or $Zr^{4+}$ metal ions, as disclosed in Yee, K., et al., Effective Mercury Sorption by Thiol-Laced Metal-Organic Frameworks: in Strong Acid and the Vapor Phase. Journal of American Chemical Society, 2013, 135 (21), p. 7795-7798, hereby incorporated by reference in its entirety. Heavier chalcogens, such as selenium and tellurium, exhibit stronger binding affinity than sulfur, but reports of selenium- and tellurium-containing MOFs have been limited and their role in the removal of mercury from hydrocarbon streams have not yet been described. Similarly, the present invention also relates to a POP that reacts with trace mercury contaminant in a hydrocarbon stream, wherein at least one of the organic monomers that defines the structure of the POP contains at least one chalcogen selected from a group consisting of sulfur, selenium, tellurium, and combinations thereof.

In another embodiment, a MOF comprises at least one organic ligand that comprises of at most one carboxylate group and at least a chalcogen that is selected from sulfur, selenium, tellurium, and combinations thereof. Organic ligands of such motif includes those that are made with the precursor thioglycolic acid, salts of thioglycolic acid, and combinations thereof. The MOF preferably comprises of at least one $Zr^{4+}$ metal ion and the incorporation of organic ligand results in a sulfur content of 2 to 22 weight percent of the MOF. The gravimetric surface area of the MOF, as defined by Brunauer-Emmett-Teller (BET) theory, is preferably in the range of 800 to 2000 $m^2/g$. The mercury uptake capacity of the MOF is between 0.5 to 15 weight percent of the MOF. The MOF material remains porous subsequent to being exposed to mercury vapor and the surface area of the material is in the range of 500 to 2,000 $m^2/g$.

Figure 1D:
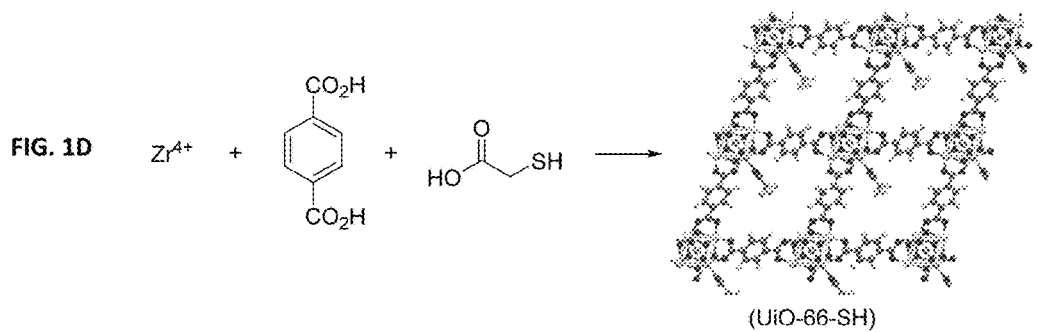

A particular example of this embodiment relates to a MOF that is a reaction product between $ZrCl_4$, terephthalic acid and thioglycolic acid (UiO-66-SH, as shown in FIG. 1D). The measured sulfur content of the MOF was 5 percent of the MOF by weight. The gravimetric surface area of the MOF, as defined by Brunauer-Emmett-Teller (BET) theory, was measured to be 1,400 $m^2/g$. After the material was exposed to mercury vapor in a closed container, the mercury uptake was measured to be 1% of the MOF by weight and the surface area of the material was measured 950 $m^2/g$.

One embodiment of this invention relates to a MOF or a POP that encapsulates a chemical specie capable of reacting with mercury through a reaction mechanism consisting of oxidation or reduction wherein the chemical specie is a chalcogen selected from a group consisting of sulfur, selenium, tellurium, and combinations thereof. In addition, the present invention relates to a MOF or a POP that encapsulates a chemical specie that is capable of forming an amalgam with mercury, wherein at least one of the chemical species is at a metal selected from a group comprising, but not limiting to aluminum, barium, copper, indium, gold, potassium, silver, sodium, strontium, rubidium, tin, zinc, and combinations thereof. The encapsulation of these reactive chemical species within pores of highly porous MOF and POP materials enables a substantial increase in the contact surface area of these active components. The preferred atomic ratio between maximum sorbed mercury and total encapsulated chemical specie to be in the range of 0.2 and 1.0.

In one embodiment, a MOF comprises of at least one $Zr^{4+}$ metal ion, at least one of the organic ligand is made with the precursor terephthalic acid and encapsulates silver that is capable of forming an amalgam with mercury. The MOF is characterized by a silver content of 5 to 20 weight percent of the MOF. The gravimetric surface area of the material, as made with Brunauer-Emmett-Teller (BET) theory, is preferred to be in the range of 600 to 2,000 $m^2/g$. The mercury uptake capacity of the material is at least 5 weight percent of the MOF. The MOF material remains porous subsequent to the exposed to mercury vapor and the surface area of the material is in the range of 500 to 2,000 $m^2/g$.

Figure 1E:
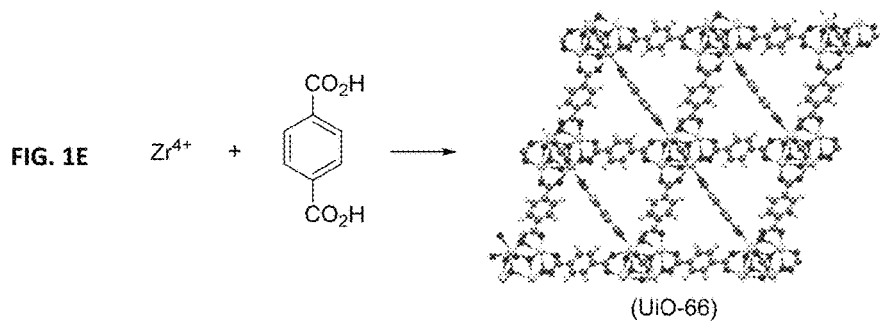

The present invention also relates a method of encapsulating silver into a MOF through the post-synthetic reaction of a precursor MOF with a silver solution. A particular example of this embodiment is the synthesis of silver-encapsulated UiO-66 (Ag@UiO-66, as shown in FIG. 1F). Porous material UiO-66 comprises the product of reaction between $Zr^{4+}$ metal ions and terephthalic acid (UiO-66, as shown in FIG. 1E). UiO-66was reacted with a silver solution resulting in an incorporated silver content measured at 8 weight percent of the total MOF. The surface area of the resulting material was 1100 $m^2/g$. After the material was exposed to mercury vapor in a closed container, the mercury uptake was measured to be 13 weight percent of the total weight of the MOF. The atomic ratio between the sorbed mercury and encapsulated chemical specie is 0.8 and the surface area of the material was measured at 710 $m^2/g$.

The ability of highly porous MOF and POP materials to encapsulate reactive chemical species can be further extended to embed sulfur-reactive components such as metal oxides. Although metal oxides do not directly react with mercury contaminants, it is understood that metal oxides can react with the sulfur component of hydrocarbon gas streams to form metal sulfides, significantly enhancing the chemisorption capacity of conventional sorbents such as active carbon. Metal oxides that are related to the this embodiment comprise a metal that is selected from a group consisting of lithium, sodium, potassium, rubidium, cesium, beryllium, magnesium, calcium, strontium, barium, scandium, yttrium, titanium, zirconium, hafnium, vanadium, niobium, tantalum, chromium, molybdenum, tungsten, manganese, rhenium, iron, ruthenium, osmium, cobalt, rhodium, iridium, nickel, palladium, platinum, copper, silver, gold, zinc, cadmium, mercury, aluminum, gallium, indium, thallium, tin, lead, bismuth, and combinations thereof. The encapsulation of these reactive chemical species within pores of highly porous MOF and POP materials enables a highly effective mercury removal sorbent in the presence of a sulfur-containing hydrocarbon stream.

In one embodiment, the MOF, POP, and combinations thereof are provided in a container through which a hydrocarbon stream flows in contact with the MOF material to substantially remove the mercury contaminants from the hydrocarbon stream and increase the purity of said hydrocarbon stream. The MOFs or POPs provided in the container can be formed in various shapes, such as pellets (as shown in FIG. 2A), disks (as shown in FIG. 2B), or a monolithic body (as shown in FIG. 2C), in a method that gives optimal diffusion characteristics, reactivity, and efficiency for the removal of mercury from the hydrocarbon stream.

Figure 5:
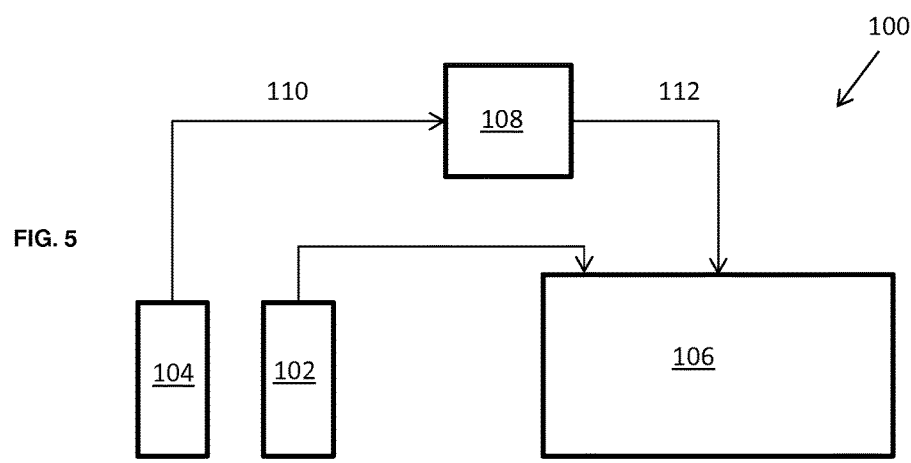
FIG. 5 is a schematic illustration of a system configured to supply purified electronic gases to a semiconductor manufacturing apparatus according to an embodiment.

FIG. 5 illustrates a system 100 configured to supply purified electronic gases to a semiconductor manufacturing apparatus 106 according to an embodiment. The system 100 includes a carrier gas vessel 102 which includes an inert carrier gas such as argon, nitrogen, helium, etc. The system 100 also includes a vessel 104 which includes an electronic gas to be used in the semiconductor manufacturing apparatus 106 and a vessel 108 which includes a MOF or POP. Contaminated electronic gas is supplied to the vessel 108 via an inlet conduit 110. In an embodiment, the MOF or POP adsorbs the electronic gas. In this embodiment, the contaminant gas is vented through a vent, not shown. When the MOF or POP is fully loaded, the temperature (temperature swing) or pressure (pressure swing) may be adjusted to release the adsorbed electronic gas. Purified electronic gas exits the vessel 108 and is provided to the semiconductor manufacturing apparatus 106 via outlet conduit 112. In an embodiment, an inert purge gas may be supplied to assist in desorbing the adsorbed electronic gas. In an alternative embodiment, the vessel 108 may include a MOF or POP suitable for adsorbing and removing the impurities from the electronic gas.

Figure 6:
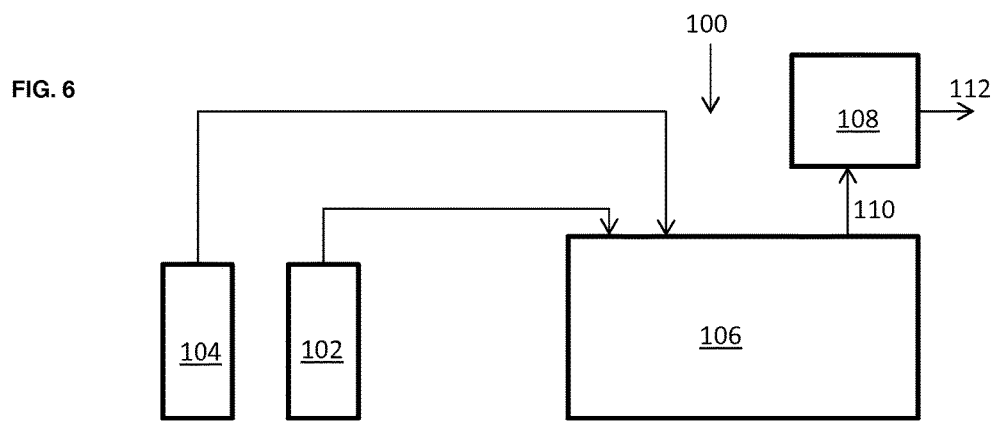
FIG. 6 is a schematic illustration of a system configured to purify electronic gases used in a semiconductor manufacturing apparatus according to an embodiment.

FIG. 6 illustrates a system 100 configured to purify electronic gases used in a semiconductor manufacturing apparatus according to another embodiment. This embodiment is similar to the previous embodiment. However, in this embodiment, the vessel 108 is configured to purify the gases exiting the semiconductor manufacturing apparatus 106. That is, the vessel 108 may be configured to separate the electronic gas from the carrier gas. For example, the MOF $Mn_2(DOBDC)$ may be used in vessel 108 to sorb phosphine or arsine. The MOF $Co_2(DOBDC)$ may be used to sorb boron trifluoride. Alternatively, the vessel 108 may be filled with the POP PAF-40 to sorb phosphine, arsine or boron trifluoride.

Figure 7:
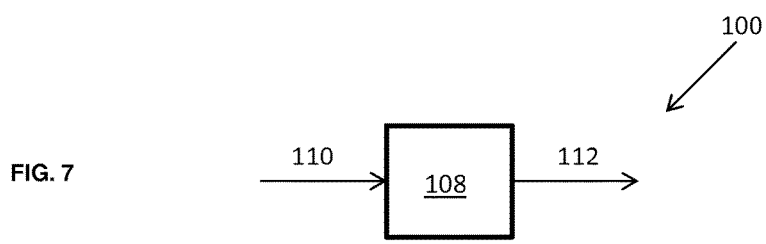
FIG. 7 is a schematic illustration of a system configured to remove mercury from a hydrocarbon stream according to an embodiment.

FIG. 7 illustrates a system configured to remove mercury from a hydrocarbon stream according to an embodiment. In this embodiment, a hydrocarbon stream contaminated with mercury is supplied to the vessel 108 via an inlet conduit 110. In embodiment, the MOF or POP includes a metal, such as silver, that forms an amalgam with the mercury and thereby removes mercury from the hydrocarbon gas stream. A purified hydrocarbon stream, e.g. a hydrocarbon stream having a lower concentration of mercury than the input stream, exits the vessel 108 via an outlet conduit 112.

The following references teach aspects of the fabrication of MOFs and are hereby incorporated by reference in their entirety:

1. Li, H., et al., Design and synthesis of an exceptionally stable and highly porous metal-organic framework. Nature, 1999. 402(6759): p. 276-279.
2. Ferey, G., Hybrid porous solids: past, present, future. Chemical Society Reviews, 2008. 37(1): p. 191-214.
3. Wilmer, C. E., et al., Large-scale screening of hypothetical metal-organic frameworks. Nature Chemistry, 2012. 4(2): p. 83-89.
4. Farha, O. K., et al., De novo synthesis of a metal-organic framework material featuring ultrahigh surface area and gas storage capacities. Nature Chemistry, 2010. 2(11): p. 944-948.
5. Furukawa, H., et al., Ultrahigh Porosity in Metal-Organic Frameworks. Science, 2010. 329(5990): p. 424-428.
6. Ferey, G., et al., A chromium terephthalate-based solid with unusually large pore volumes and surface area. Science, 2005. 309(5743): p. 2040-2042.
7. Chae, H. K., et al., A route to high surface area, porosity and inclusion of large molecules in crystals. Nature, 2004. 427(6974): p. 523-527.

8. Wilmer, C. E., et al., Structure-property relationships of porous materials for carbon dioxide separation and capture. Energy & Environmental Science, 2012. 5(12): p. 9849-9856.
9. Wu, D., et al., Design and preparation of porous polymers. Chemical Review, 2012, 112(7): p. 3959.
10. Farha, O. K., et al., Metal-Organic Framework Materials with Ultrahigh Surface Areas: Is the Sky the Limit? Journal of the American Chemical Society, 2012, 134(36): p. 15016-15021.
11. Nelson, A. P., et al., Supercritical Processing as a Route to High Internal Surface Areas and Permanent Microporosity in Metal-Organic Framework Materials. Journal of the American Chemical Society, 2009, 131(2): p. 458.
12. Li, J., et al, Selective gas adsorption and separation in metal-organic frameworks. Chemical Society Review, 2009, 38: p. 1477-1504.
13. Lu, W., et al., Porous Polymer Networks: Synthesis, Porosity, and Applications in Gas Storage/Separation. Chemistry of Materials, 2010, 22(21): p. 5964-5972.
14. Yee, K., et al., Effective Mercury Sorption by Thiol-Laced Metal-Organic Frameworks: in Strong Acid and the Vapor Phase. Journal of American Chemical Society, 2013, 135(21), p. 7795-7798.
15. Weston, M. H., et al., Phosphine Gas Adsorption in a Series of Metal-Organic Frameworks. Inorganic Chemistry, 2015, 54(17): p. 8162-8164.

Although the foregoing refers to particular preferred embodiments, it will be understood that the invention is not so limited. It will occur to those of ordinary skill in the art that various modifications may be made to the disclosed embodiments and that such modifications are intended to be within the scope of the invention. All of the publications, patent applications and patents cited herein are incorporated herein by reference in their entirety.

What is claimed is:

1. A system comprising:
    a vessel filled with a material configured for abatement of electronic gases comprising:
        a metal organic framework (MOF) comprising the coordination product of a plurality of metal clusters, each metal cluster comprising one or more metal ions, and a plurality of multidentate organic ligands that connect adjacent metal clusters, wherein the one or more metal ions and the organic ligand are selected to provide reactivity with or sorptive affinity toward electronic gas to substantially remove or abate electronic gas in an electronic gas-containing effluent; or
        a porous organic polymer (POP) comprising a polymerization product from at least a plurality of organic monomers, wherein the organic monomers are selected to provide reactivity with or sorptive affinity towards electronic gas to substantially remove or abate electronic gas in an electronic gas-containing effluent;
    a semiconductor manufacturing apparatus; and
    a conduit connecting the vessel with an output of the semiconductor manufacturing apparatus.

2. The system of claim 1, wherein the MOF or POP are configured in a bed.

3. The system of claim 1, wherein the semiconductor manufacturing apparatus comprises at least one of a chemical vapor deposition apparatus, atomic layer deposition apparatus or ion implantation apparatus.

4. A material configured for purification of electronic gases comprising:
    a metal organic framework (MOF) comprising the coordination product of a plurality of metal clusters, each metal cluster comprising one or more metal ions, and a plurality of multidentate organic ligands that connect adjacent metal clusters, wherein the one or more metal ions and the organic ligand are selected to provide reactivity with or sorptive affinity towards contaminants in a stream of electronic gas to substantially remove the contaminants from a stream of electronic gas and increase the purity of said electronic gas; or
    a porous organic polymer (POP) comprising a polymerization product from at least a plurality of organic monomers, wherein the organic monomers are selected to provide reactivity with or sorptive affinity towards contaminants in a stream of electronic gas to substantially remove the contaminants from a stream of electronic gas and increase the purity of said electronic gas,
    wherein the electronic gas is selected from a group consisting of arsine, boron trichloride, boron trifluoride, diborane, phosphine, and combinations thereof; and
    wherein the MOF or POP encapsulates chemical species that are reactive towards contaminant.

5. The material of claim 4, wherein the chemical species is selected from a group consisting of basic species, acidic species, hydrolyzing species, oxidants, reductants, and combinations thereof.

6. A system comprising:
    a vessel filled with a material configured for purification of electronic gases comprising:
        a metal organic framework (MOF) comprising the coordination product of a plurality of metal clusters, each metal cluster comprising one or more metal ions, and a plurality of multidentate organic ligands that connect adjacent metal clusters, wherein the one or more metal ions and the organic ligand are selected to provide reactivity with or sorptive affinity towards contaminants in a stream of electronic gas to substantially remove the contaminants from a stream of electronic gas and increase the purity of said electronic gas; or
        a porous organic polymer (POP) comprising a polymerization product from at least a plurality of organic monomers, wherein the organic monomers are selected to provide reactivity with or sorptive affinity towards contaminants in a stream of electronic gas to substantially remove the contaminants from a stream of electronic gas and increase the purity of said electronic gas;
    a semiconductor manufacturing apparatus; and
    a conduit connecting the vessel with an inlet of the semiconductor manufacturing apparatus.

7. The system of claim 6, wherein the MOF or POP are configured in a bed.

8. The system of claim 6, wherein the semiconductor manufacturing apparatus comprises at least one of a chemical vapor deposition apparatus, atomic layer deposition apparatus or ion implantation apparatus.

9. The system of claim 1, wherein the vessel is filled with the MOF having the one or more metal ions and the organic ligand selected to provide reactivity with or sorptive affinity toward the electronic gas selected from arsine, boron trichloride, boron trifluoride, diborane, phosphine, and combinations thereof.

10. The system of claim 6, wherein the vessel is filled with the MOF having the one or more metal ions and the organic ligand selected to provide reactivity with or sorptive affinity toward the contaminants in the stream of electronic gas selected from arsine, boron trichloride, boron trifluoride, diborane, phosphine, and combinations thereof.

* * * * *